United States Patent [19]
Rump et al.

[11] Patent Number: 5,793,645
[45] Date of Patent: Aug. 11, 1998

[54] METHOD OF OPERATING A VENTILATION SYSTEM ESPECIALLY OF A MOTOR VEHICLE

[75] Inventors: Hanns Rump, Unna; Jörg Hiller, Wetter; Norbert Pieper, Selm, all of Germany

[73] Assignee: I.T.V.I. International Techno Venture Invest Aktiengesellschaft, Vaduz, Liechtenstein

[21] Appl. No.: 602,753

[22] PCT Filed: Aug. 18, 1994

[86] PCT No.: PCT/EP94/02742

§ 371 Date: Feb. 13, 1996

§ 102(e) Date: Feb. 13, 1996

[87] PCT Pub. No.: WO95/05949

PCT Pub. Date: Mar. 2, 1995

[30] Foreign Application Priority Data

Aug. 21, 1993 [DE] Germany .............. 43 28 218.0

[51] Int. Cl.⁶ .................................................. G01N 31/00
[52] U.S. Cl. .............. 364/505; 364/506; 364/551.01; 73/23.2; 73/23.31; 73/31.05; 422/94; 422/98
[58] Field of Search .................... 364/505, 551.05; 340/632; 454/69, 165; 422/94, 98; 73/23.2, 23.31

[56] References Cited

U.S. PATENT DOCUMENTS

| | | | |
|---|---|---|---|
| 4,930,407 | 6/1990 | Hölter et al. | 454/75 |
| 4,992,965 | 2/1991 | Hölter et al. | 364/551.01 |
| 5,054,686 | 10/1991 | Chuang | 236/49.3 |
| 5,120,271 | 6/1992 | Shtanko | 454/137 |
| 5,167,129 | 12/1992 | Akasaka | 62/179 |
| 5,178,121 | 1/1993 | Kitajima et al. | 123/689 |
| 5,217,692 | 6/1993 | Rump et al. | 422/98 |
| 5,256,103 | 10/1993 | Abthoff et al. | 454/139 |
| 5,311,783 | 5/1994 | Takeuchi | 73/865.5 |
| 5,320,577 | 6/1994 | Tooru et al. | 454/75 |
| 5,576,739 | 11/1996 | Murphy | 340/825.06 |
| 5,629,474 | 5/1997 | Williams | 73/23.2 |

*Primary Examiner*—Emanuel Todd Voeltz
*Assistant Examiner*—Demetra Smith
*Attorney, Agent, or Firm*—Herbert Dubno

[57] ABSTRACT

The previously presented teaching of the invention describes a method for the evaluation of sensor signals with the purpose of producing plausible and physiologically satisfying switching impulses for interrupting or for opening the air supply in ventilation systems, particularly for the ventilation of passenger cabins in motor vehicles, depending on the pollutant content of the ambient air established by one or more sensors.

10 Claims, 3 Drawing Sheets

METHOD OF OPERATING A VENTILATION SYSTEM ESPECIALLY OF A MOTOR VEHICLE

CROSS REFERENCE TO RELATED APPLICATIONS

This application is a national phase application of PCT/EP94/02742 filed Aug. 18, 1994 and based, in turn on German application P 43 28 218.0 of Aug. 21, 1993 under the International Convention.

FIELD OF THE INVENTION

The present invention relates to the use of sensors for the purpose of triggering an electric impulse when there are increased concentrations of gases (target gases) to which the sensor element or elements sensitive. (=target gases).

More particularly, an application of the invention is interruption of the air supply to a motor vehicle cabin when due to the emissions of other vehicles, there is an increased concentration of noxious or toxic gases such as carbon monoxide, nitrogen oxides, sulfur dioxide, partially burnt hydrocarbons, etc. in the air supply to the vehicle cabin.

BACKGROUND OF THE INVENTION

It is known to use various sensors for detecting concentrations of various gases, for instance:

| | |
|---|---|
| Tin dioxide ($SnO_2$) | for all oxidizable gases |
| Phthalocanine | for reducible gases |
| Tungsten trioxide ($WO_3$) | for nitrogen oxides. |

For the evaluation of the signals it is known to trigger the switching signal not when an absolute level is reached, but rather then when the sensor or sensors detect an increased concentration of the target gas in relation to the average level.

Since the sensors are subject to a certain drift, being mostly cross-sensitive with respect to air humidity, and have to operate in areas with very different basic pollutant levels, it has been proposed to differentiate the sensor signal from the background via an electric high pass filter so that the noxious substances resulting from other motor vehicles give rise to clearly differentiated switching pulses to contrasted with the above-mentioned background effects. If the basic frequency of the high-pass filter is selected so that in contrast to the slower changes these pulses (target impulses) are transmitted, each relevant deterioration of the level of noxious substances will advantageously lead to a switching signal. It has been further proposed to differentiate the signal many times, so that even smaller signal changes can be evaluated (see EP 87 00 592).

Since, as a rule, sensors react quickly to a target gas, but are significantly slower in restoring to the initial value, this method is only satisfactory for generating the command "interrupt air supply", but the cancellation command "reopen air supply" is not produced as satisfactorily.

It is known to continuously build up the average value of the sensor signal over a certain time period (e.g. for 10 minutes) and to compare the actual (instantaneous) sensor value with this average value. The signal "close air supply", as well as the signal "open air supply" can be derived therefrom satisfactorily. Details are described in EP 87 00 592 from 1986/87. However for this method sensor signals of a certain amplitude are required. In the case of very small sensor signals, uncertainties in their evaluation occur.

SUMMARY OF THE INVENTION

According to the invention it is therefore proposed to factor in the signal changes as such for evaluation, whereby the consideration of behavior over time plays an essential part.

In particular, the method for evaluating sensor signals has the purpose of generating switching pulses which, via suitable setting elements and air supply ducts, influence the air supply to an inner space, preferably the cabin of a motor vehicle. The air supply is interrupted in the presence of a gas concentration representing a switching criterium or the supplied air is passed through a filter system before it reaches the inner space, i.e. the supply of air from a particular source is cutoff. The initial state is restored, i.e. air supply from the original source is restored, when the quality of the ambient air improves.

When the sensors have an electrical resistance which reduces in the presence of the target gas, an integral is formed from the actual sensor value over a free determined time period which is reduced by a value (x) with the free air supply being interrupted as soon as the actual sensor value falls below the threshold formed by the integral reduced by the value (x). The switching signal can also be triggered when the electronic evaluation system determines that the change rate of the sensor signal in a free determinable time period is greater than a free determined value (y).

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
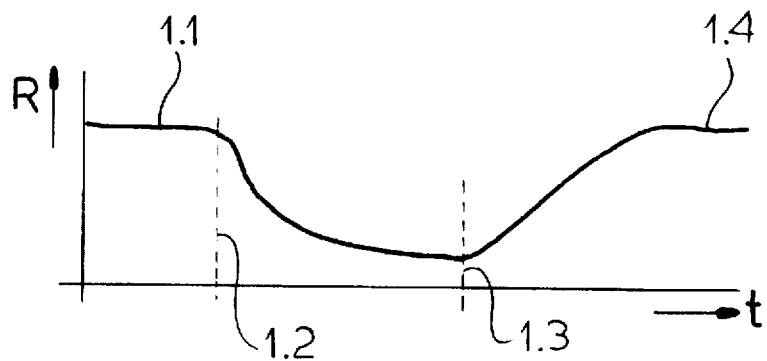
FIG. 1 is a graph of resistance versus time illustrating the characteristic curve of a sensor responding to the development of a target gas concentration in the ambient air to be supplied to a close space.

FIG. 1 shows a change in a typical sensor signal provoked by target gases. At 1.1 the sensor is less subject to pollutants (normal air value). The content of target gases in the air starts at the point of time 1.2. Here a negative gradient can be reliably detected and has a slope which is clearly greater than the normal variations. During the presence of target gases the sensor is in the area 1.3. When the pollutant content of the air returns to normal, an increase in the sensor value can be at first noticed at 1.3, whereby after a while the initial value 1.4 is reached.

It is thus advisible to interrupt the air supply at the point in time 1.2 and to restore it again at the point in time 1.3. In the example a sensor is used whose electric resistance drops under by the action of the target gases.

In principle the above applies also when the sensor has the reverse characteristic, which means that its resistance increase in the presence of the target gas.

However in practice the sensor signals are rarely so clear cut, so that the signal processing has to meet higher demands.

In the preferred embodiment (FIG. 2) the evaluation of the sensor signals 2.4 takes place in a program-controlled microcomputer 2.3, with the signals from the sensor 2.1 being digitized in an analog/digital converter 2.2.

Figure 3:
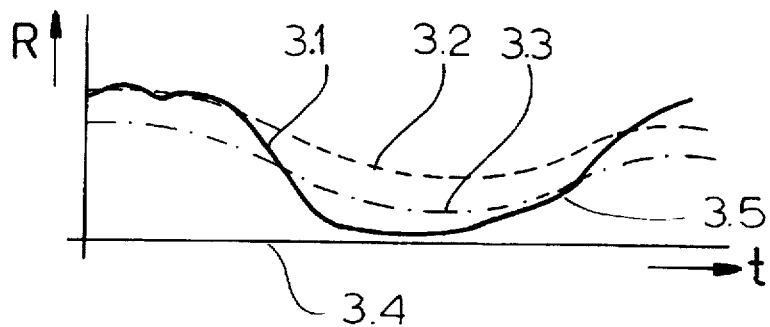
FIGS. 3 through 8 are graphs of resistance versus time showing various embodiments of control according to the invention.

FIG. 3 shows the principle of the invention in a very simplified manner. The sensor signal is shown at 3.1 and by nature has comparatively small variations. The curve 3.2 is a mathematical average value (integral) of the signal 3.1, whereby the integration time can be freely determined and as a rule is 5–10 min. The curve 3.3 is a computer-created curve which has numerical values which are lower by a small amount (=x) than the curve 3.2. The amount x can be a fixed amount or it can be a proportional factor or e.g. 1% of the curve 3.2.

The air supply is interrupted at a point in time 3.4, when the curve 3.1 assumes a lower value than the curve 3.3 and is again opened when the value 3.1 is again greater than the value 3.3. It can be thereby noticed that the integration time has a considerable influence.

If the integration time is relatively short, the ventilation would be restored even though there was an objectively high level of noxious substances. On the contrary, if the integration time is very long, in some situations the closing time will also be subjectively too long.

Figure 4:
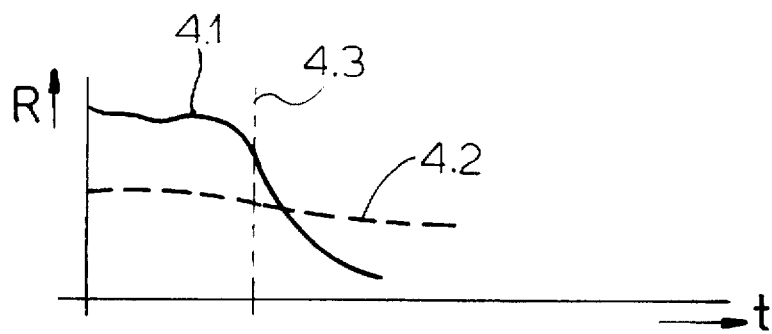

Very high concentrations of target gases generate in the sensor, at the moment of detection, a very quick signal change. For this situation the invention proposes advantageously to always trigger an additional switching signal when the differential rate of the sensor signal over time is greater than a certain predetermined value (y), independently of the fact whether the switching condition previously described in FIG. 3 is met. FIG. 4 describes the principle:

The sensor value 4.1 undergoes a quick change when subjected to the action of the target gas. Before it reaches the threshold 4.2 the following is established by the evaluation computer 2.3:

$$\Delta s/\Delta t>y$$

In this way a further switching condition is met and the switching impulse is triggered.

In the explanation of FIG. 3 it was noted that the cancellation of the closing command, i.e. the command "admit air supply" functions with the described method, but in certain situations remains physiologically and objectively unsatisfactory.

Figure 5:
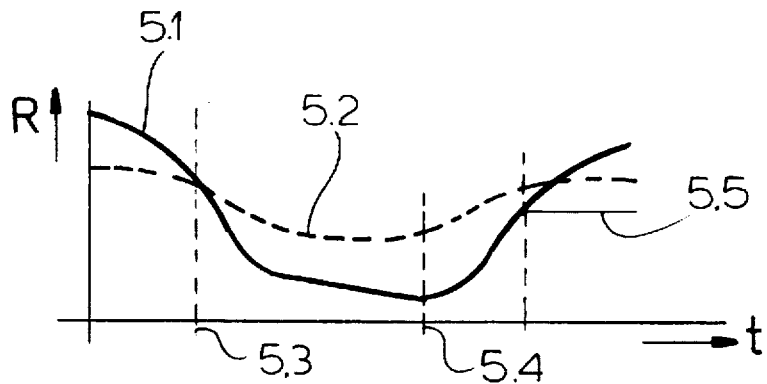

FIG. 5 shows an advantageous solution. The curve 5.1 is the curve representing the actual sensor signal and the curve 5.2 is the integral of the sensor signal minus x. At the point of time 5.3 the air access is interrupted. At the point in time 5.4 the sensor value has achieved a positive gradient. The criterium for opening the air supply is met when the actual sensor value, starting out from the point in time 5.4, reaches a value 5.5, increased by the value y. Thus the integration time is no longer the only defining factor of the switching behavior. The invention uses to its advantage the observation that the human olfactory organ can adapt to "bad air", and basically reacts only to changes in the air composition, or the air pollutant content.

If the arrangement according to the invention reacts to a so-called "fresh air pulse", independently of the objective air quality, this will be acceptable as to the human nose.

Figure 6:
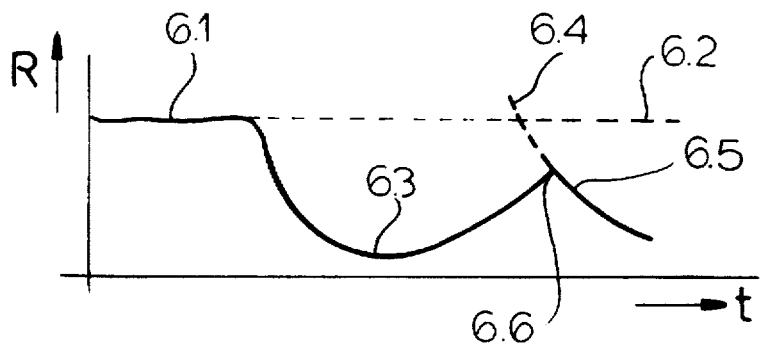

FIG. 6 shows a system of this latter type. In pollutant-free air the sensor assumes the value 6.1. In the presence of the target gas the value 6.3 is reached. The initial value (fresh air level) is shown in broken lines as 6.2. Now the sensor is subjected to a further pulse of noxious substances and produces the reaction 6.5. The reaction, which seems insignificant at a first glance, in fact represents the result of an pulse of noxious substances, similar to 6.3. However this pulse 6.5 hit on a sensor in the desorption phase 6.6. If the starting point was the fresh air level 6.2, than a signal similar to 6.4 would have been registered, whose greater gradient would have met the switching criterium described in FIG. 4.

Therefore in accordance with the invention the computer 2.3 establishes at all times the value and direction of the respective slope. In the desorption phase 6.6 a positive change rate of D1 is found. At the moment of gas impulse it comes to direction reversal and the now negative change rate equals D2 at 6.5. The computer program now adds the absolute values of the two change rates $$abs (D1)+abs (D2)=D3$$

D3 is the change rate to be evaluated. The program checks now whether the change rate is greater than a value y, which would lead to turning off the air supply without delay. Depending on the characteristics of the used sensor element, and particularly on its time lag in the desorption phase 6.6., it is proposed to multiply the change rate D1 by a factor, in order to obtain with D3 a value which corresponds to the change rate 6.4 in the case of the nondesorbing sensor.

Figure 7:
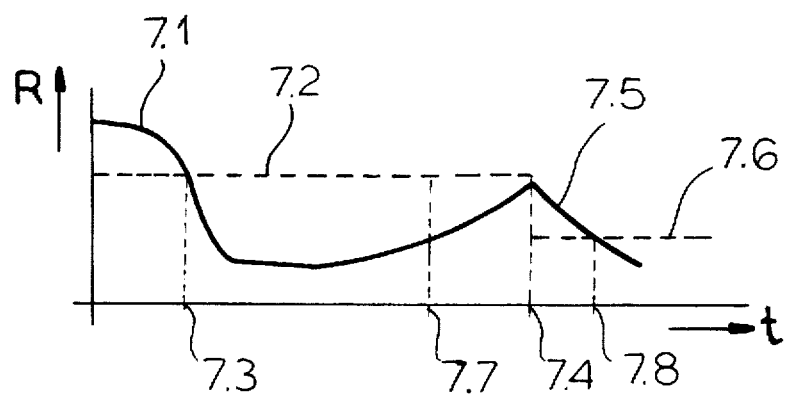

With the previously described teaching a satisfactory switching behavior is achieved in most cases. Especially then when pulses of the target gas are directed in quick succession onto the sensor or sensors, the resulting situations are not always satisfactory and plausible. For this reason the method of control is effected according to FIG. 7 as followed is proposed:

The initial sensor value is 7.1, which diminishes in the presence of the target gas and at the point of time 7.3 falls below the value 7.2 resulted from the integral, thereby fulfilling the switching criterium. Without target gas the sensor recovers again and shows a positive gradient, which at the point in time 7.7, has reached the value y, which triggers the switching impulse (open air supply). At the point of time 7.4 a reversal of the gradient can be seen, which is caused by a new occurrence of the presence of target gas. At this moment the comparative value 7.2 is set to the value 7.6, which is the actual sensor value at the point of time 7.4 lowered by the rate x known from FIG. 3.

At the point of time 7.8 the actual sensor rate runs through the curve 7.6 and thereby triggers again the switching signal "interrupt air supply".

Figure 8:
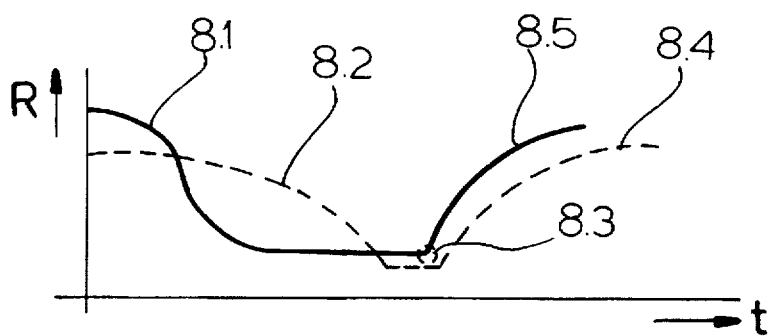

In the method of the invention illustrated in FIG. 8, the formation of the comparative value 8.2 and 8.4 is made dependent on the rate and direction of the gradient assumed by the actual sensor value 8.1 and 8.5. The reason for that is the observation that certain sensors have a clearly longer desorption phase compared to the adsorption phase.

In the desorption phase the integration takes place mostly in the sensor itself, so that a further integration makes the resetting of the of the comparative value too slow. According to the invention, we create the comparative value 8.4 after the direction reversal of the gradient 8.3 either directly from the actual sensor value, diminished by a value x, or from an integral with reduced integration time. If the rate of the gradient is smaller than a freely selected value, then again the integration of the sensor values takes place over a longer time span.

Figure 2:
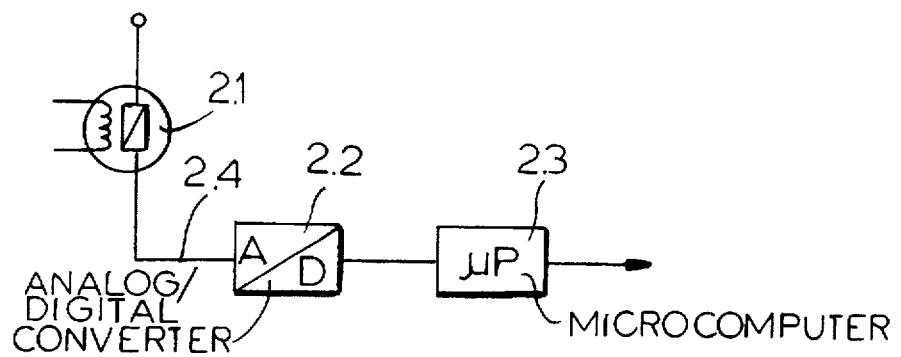
FIG. 2 is a block diagram of a control system according to the invention.

The teaching of the invention is advantageously applied in a version according to FIG. 2, whereby the execution is assigned to a program-controlled microprocessor as a purely mathematical operation.

We claim:

1. A method of operating a ventilation system, comprising the steps of:

(a) supplying air to a space to be ventilated and formed by a cabin of an automotive vehicle;

(b) detecting a concentration of a target gas in air to be supplied to said space and generating an actual value electrical signal as a measure of said concentration;

(c) automatically forming an integral value by integrating said actual value signal over a selected time period;

(d) automatically generating a switching signal and cutting off supply of said air to said space with said switching signal selectively upon:

($d_1$) said actual value signal varying through a first threshold determined by said integral value and in a direction representing a certain increased concentration of said target gas, and ($d_2$) a rate of change of said actual value signal in said direction over a preselected time interval exceeds a preselected value;

(e) automatically canceling said switching signal and restoring supply of said air to said space upon a change in said actual value signal in an opposite direction; and (f) monitoring a gradient in said actual value signal after cancellation of said switching signal and restoration of supply of air to said space and, upon reversal of said gradient, adding an absolute value of the negative gradient to an absolute value of the positive gradient, and triggering a switching pulse to again cut off flow of air to said space when the sum of absolute values of said gradients is greater or said actual value signal is less than said further value.

2. The method defined in claim 1 wherein the concentration of said target gas is detected with a sensor which has reduced electrical resistance as the concentration of said target gas increases and said switching signal is automatically generated when said actual value signal falls below the integral value diminished by a predetermined value (x) and the switching signal is cancelled and supply of air is restored to said space upon a rise of said actual value signal said actual value signal being a signal representing said resistance.

3. The method defined in claim 1 wherein said concentration of said target gas is detected in air supplied to said space with a sensor which increases electrical resistance in the presence of the target gas and said switching signal is generated when said actual value signal rises to said integral value and said rate of change is a positive gradient.

4. The method defined in claim 1 wherein said switching signal is cancelled and supply of said air to said space is restored upon a rise in said actual value signal to a threshold representing said integral value reduced by an amount (x).

5. The method defined in claim 1 wherein said switching signal is cancelled and supply of said air to said space is restored when a signal from a sensor measuring said concentration is reversed by desorption at said sensor, an actual sensor signal is stored in an electronic evaluation system and is increased by an amount to a switching level and the supply of air to said space is restored when the actual value signal rises above a second threshold corresponding to said switching level.

6. The method defined in claim 1 wherein a sensor is added for the measurement of concentration of said target gas which reverses in signal output upon desorption, an actual sensor signal at desorption is stored and the stored signal is increased by a certain amount of to a switching level and said switching signal is automatically cancelled and supply of air to said space is restored upon the actual value signal falls below a threshold determined by said switching level for a sensor which has increased resistance in the presence of said target gas.

7. The method defined in claim 1 wherein formation of said integral value is interrupted when the gradient of said actual value signal becomes negative in a case in which said sensor is a sensor measuring said concentration and having a resistance increasing with the presence of said target gas and, when said gradient is negative, said threshold is formed from the actual sensor value plus a value (x).

8. The method defined in claim 1 wherein said threshold is determined by deducting a value (x) from the integral value and, upon a reversal of a gradient of said actual value signal, the integration duration is shortened with a longer normal integration time being restored when said gradient is represented by a quotient smaller than a given value.

9. A method of operating a ventilation system, comprising the steps of:

(a) supplying air to a space to be ventilated and formed by a cabin of an automotive vehicle;

(b) detecting a concentration of a target gas in air to be supplied to said space and generating an actual value electrical signal as a measure of said concentration;

(c) automatically forming an integral value by integrating said actual value signal over a selected time period;

(d) automatically generating a switching signal and cutting off supply of said air to said space with said switching signal selectively upon:

($d_1$) said actual value signal varying through a first threshold determined by said integral value and in a direction representing a certain increased concentration of said target gas, and ($d_2$) a rate of chance of said actual value signal in said direction over a preselected time interval exceeds a preselected value;

(e) automatically canceling said switching signal and restoring supply of said air to said space upon a change in said actual value signal in an opposite direction; and (f) monitoring a gradient in said actual value signal after cancellation of said switching signal and restoration of supply of air to said space and, upon reversal of said gradient, adding absolute value of the negative gradient to an absolute value of the positive gradient and triggering a switching pulse to again cut off flow of air to said space when the sum of absolute values of said gradients is smaller than a further valve or said actual value signal is greater than said further value.

10. A method of operating a ventilation system, comprising the steps of:

(a) supplying air to a space to be ventilated and formed by a cabin of an automotive vehicle;

(b) detecting a concentration of a target gas in air to be supplied to said space and generating an actual value electrical signal as a measure of said concentration;

(c) automatically forming an integral value by integrating said actual value signal over a selected time period;

(d) automatically generating a switching signal and cutting off supply of said air to said space with said switching signal selectively upon:

($d_1$) said actual value signal varying through a first threshold determined by said integral value and in a direction representing a certain increased concentration of said target gas, and ($d_2$) a rate of change of said actual value signal in said direction over a preselected time interval exceeds a preselected value;

(e) automatically canceling said switching signal and restoring supply of said air to said space upon a change in said actual value signal in an opposite direction; and (f) interrupting said integral value when a gradient of the actual value signal becomes positive in a case in which said concentration is measured with a sensor having a reduced resistance in the presence of said target gas and, when said gradient is positive, forming a threshold by deducting an amount (x) from the actual sensor value.

* * * * *